United States Patent [19]

Aalvik Thune

[11] Patent Number: 5,007,413
[45] Date of Patent: Apr. 16, 1991

[54] SUPPORTING DEVICE FOR USE IN FIRST AID TO PERSONS INJURED IN ACCIDENTS OR THE LIKE

[76] Inventor: Halldis Aalvik Thune, Loveien 30, 3500 Honefoss, Norway

[21] Appl. No.: 9,327
[22] PCT Filed: Apr. 17, 1986
[86] PCT No.: PCT/NO86/00031
  § 371 Date: Dec. 11, 1986
  § 102(e) Date: Dec. 11, 1986
[87] PCT Pub. No.: WO86/05968
  PCT Pub. Date: Oct. 23, 1986

[30] Foreign Application Priority Data

Apr. 18, 1985 [NO] Norway ............................ 851560
Nov. 22, 1985 [NO] Norway ............................ 854673

[51] Int. Cl.⁵ ............................................. A61F 5/02
[52] U.S. Cl. ............................................. 128/78; 128/870
[58] Field of Search ................. 2/44, 45; 128/89 R, 128/78, 95, 96, 97, 98, 99–102, 870

[56] References Cited

U.S. PATENT DOCUMENTS

| | | | |
|---|---|---|---|
| 1,301,276 | 4/1919 | Kroetz | 128/78 |
| 3,420,230 | 1/1969 | Ballard | 128/78 X |
| 3,570,480 | 3/1971 | Stubbs | 128/78 |
| 3,620,211 | 11/1971 | Goodell et al. | 128/78 X |
| 3,889,668 | 6/1975 | Ochs et al. | 2/44 X |
| 4,261,349 | 4/1981 | Lambson et al. | 128/89 R |
| 4,397,046 | 8/1983 | Steiner | 2/44 |
| 4,492,225 | 1/1985 | Picolet et al. | 128/89 R X |

FOREIGN PATENT DOCUMENTS 251685 9/1960 Australia .................................. 2/44

Primary Examiner—Robert A. Hafer
Assistant Examiner—Kevin G. Rooney
Attorney, Agent, or Firm—Wenderoth, Lind & Ponack

[57] ABSTRACT

A supporting device for use in first aid to persons injured in accidents or the like, in particular in cases of neck and/or back injuries, includes a main part for arrangement at the back of the injured person and provided with fastening members for anchoring. The main part and the fastening members are made generally of a flexible material. The main part is provided with an elongate supporting element adapted primarily to give support along the back and/or the neck. The supporting element has the form of a flat metal rod adapted to be detachable and insertable at or in the main part. A preferably upwardly open pocket is provided for this purpose. The main use of such a supporting device is in first aid equipment.

6 Claims, 3 Drawing Sheets

SUPPORTING DEVICE FOR USE IN FIRST AID TO PERSONS INJURED IN ACCIDENTS OR THE LIKE

This invention relates to a supporting device for use in first aid to persons injured by accidents or the like, particularly in cases of neck and/or back injuries, comprising a main part primarily adapted to be arranged centrally along the back of the person and provided with fastening means for mounting around the abdominal and chest area of the person, preferably also around the head and/or the neck, said main part with fastening means being mainly made of a flexible material and the main part comprising an elongate supporting member, in particular for supporting the back and/or the neck.

Especially in traffic accidents many neck or back injuries occur. These injuries result from traffic accidents in particular by serious collisions or when a car is hit by another from the rear. The body of the person is usually held by seat belts whereas the head and the neck are free. By a very sudden deceleration the head will be thrown abruptly and with a strong force forwardly in a front collision, and correspondingly in the backward direction when a car is hit from behind. These sudden and uncontrolled movements very often will result in neck injuries. There may also be caused injuries in the spinal column below the neck, in particular by very powerful front collisions or when a car is hit by another from the side.

Also when carrying out various work operations there may be neck and back injuries, for example in fall accidents, collapsing of constructions and the like. Injuries of this kind may also result from sport and athletic activities.

If there is any suspicion to the effect that an injured person has back or neck injuries, an attempt must be made to bring the person to treatment without subjecting the neck and the back to significant flexing. This of course may represent big problems, for example if an injured person is clamped in a damaged car, underneath building parts, avalanche masses and the like. After such accidents there will often only be present persons being relatively unskilled in medicine, and it will be necessary for these persons to flex and pull the injured person so as to have him loosened from the parts or mass in which he is clamped. Under such circumstances an injured person may easily get additional and more serious injuries during the rescue operation, than from the actual accident A high degree of flexing and twisting of an injured back or spinal column may easily result in paralysis.

When giving first aid to such injured persons it is therefore important to have at hand aiding means which may prevent the back from being flexed or twisted to an undue extent.

There are known supporting members for the neck and back of persons having been injured. From Published German Patent Application No. 2,038,769 for example, there is known a rigid supporting rod which by means of flexible bands or belts may be attached to the head and to the upper part of the body. Other examples of such supporting arrangements are found in Published German Patent Application No. 2,017,126. For a very specific type of therapeutic treatment there is known, from Published German Patent Application No. 21 43 781, a broad textile belt having pockets at the back portion for accommodating supporting elements This known device, however, is not intended for nor suitable for use in first aid operations.

SUMMARY OF THE INVENTION

The present invention is directed to substantial improvements in such devices, inter alia so as to make possible and more easy complete and accurate X-ray investigations of a patient having back or neck injuries after an accident.

This is obtained according to the invention, in a supporting device as stated above, by the provision of a supporting member consisting of a flat metal rod being arranged detachably and insertable at or in the main part.

In addition to being advantageous in connection with X-ray investigations, the device according to the invention involves advantages also with respect to a secure and stable supporting effect for the patient without having any discomfort or nuisance from the device as such. Moreover, the device may be adapted for providing support or fixation in certain positions of other body parts than the back and the neck. Besides, the device has the advantage that in very many cases it may be attached to a clamped or lying injured person without any need of moving or lifting the person.

In many cases, however, it will be difficult to insert the fastening members or bands behind a patient lying on the ground or being pressed for example against a car seat after a collision. In order to have the bands or belts put around the injured person attempts must be made to move the injured person away from the ground or car seat, and this may result in additional injury.

Thus, according to another aspect of this invention, particular solutions to this problem are proposed, as will appear from the following description.

BRIEF DESCRIPTION OF THE DRAWINGS

The invention is further explained below with reference to the drawings, in which.

DETAILED DESCRIPTION OF THE INVENTION

Figure 1:
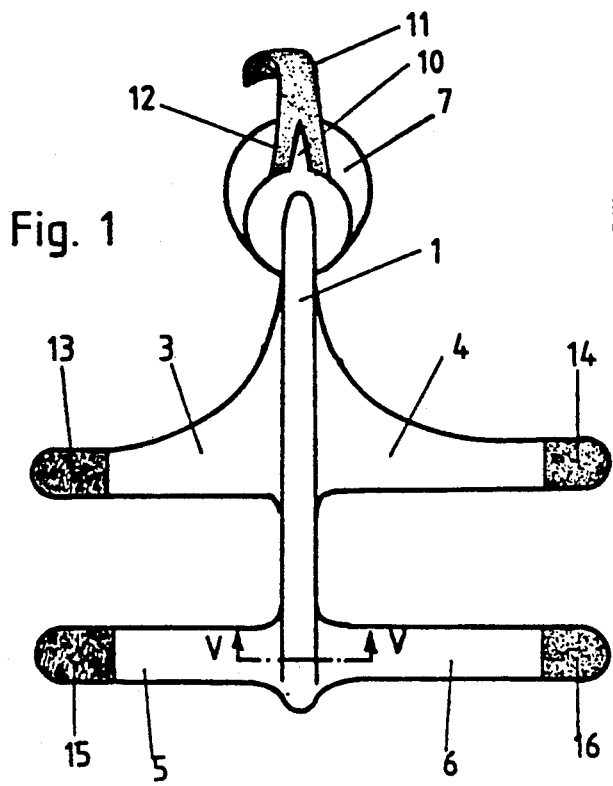
FIG. 1 is a plan view of a first embodiment of the device according to the invention.
Figure 2:
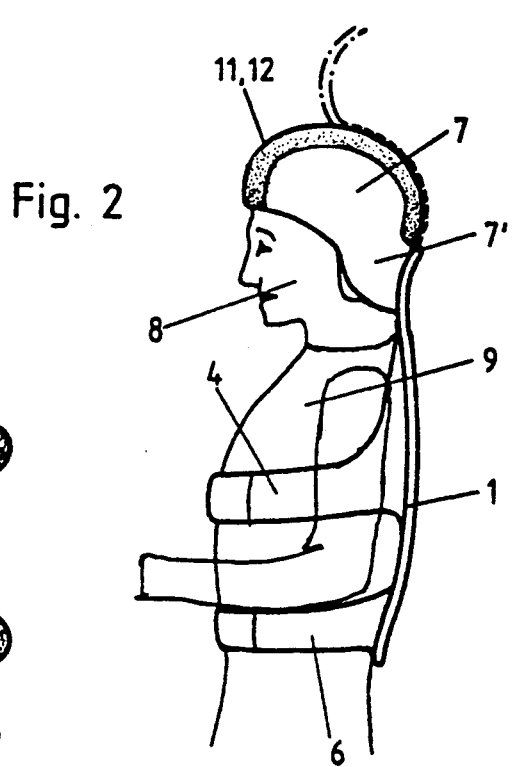
FIG. 2 is a side view of the device of FIG. 1 shown in use on an injured person.
Figure 3:
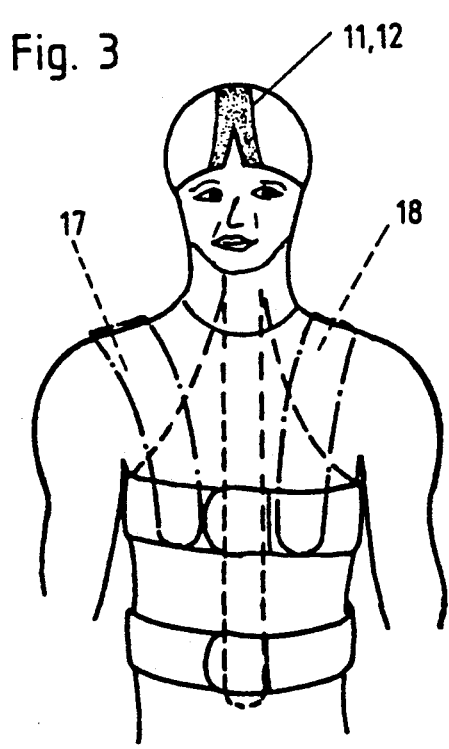
FIG. 3 is a front view of the arrangement of FIG. 2.
Figure 5:
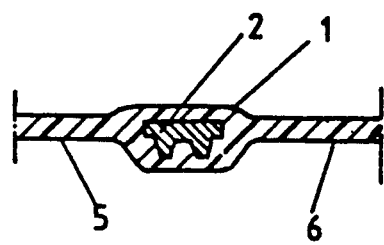
FIG. 5 is a partial section according to the line V—V in FIG. 1.

The device according to the invention as shown in FIGS. 1, 2 and 3 of the drawings, has a main part in the form of a rigid back support member 1, being preferably made of a suitable plastic material. In order to increase the stiffness of the support member this may be reinforced with a metal rod 2 or the like. An example of a possible cross-sectional shape of such metal reinforcement 2, is shown in FIG. 5. Most preferably this metal rod is relatively flat and adapted to be easily removed from the main part, as will be described in more detail in connection with FIGS. 7 and 8 below. As integral portions of the main part 1 there are provided transverse fastening members 3, 4, 5 and 6. To the upper end of main part 1 there is rigidly attached a helmet-like fastening piece 7 for attaching the main part securely to the head 8 of an injured person 9. The helmet-like fastening member has a slit 10 from the forward edge and backwards at least to the middle of the head. In this way the fastening member 7 may quite simply by means of "VELCRO" or similar type fasteners 11, 12 be adapted to the head shape and size of the injured person. In connection with accidents there will also often be head injuries and then it will be of interest to apply a compress or the like. This will then be kept in position by the helmet-like fastening member 7. Because of the slit 10 the helmet 7 may also easily be adjusted so as to accommodate a relatively thick bandage or compress.

As mentioned the fastening members 3, 4, 5, 6 are in the embodiment according to FIG. 1, made in a single integral piece of the same material as the main part or member 1, i.e. of a suitable plastic material. The material shall be resilient and flexible, but nevertheless with such a degree of stiffness that the fastening members may be inserted between the back of an injured person and the surface against which the patient is lying or is pressed against, so that the ends of the fastening members may be put around the injured person thereby making it possible to pull or push the main part 1 behind the person without any necessity of flexing or pulling the person. When the main part 1 has been brought in position along the neck and back of the person the fastening members 3, 4, 5, 6 are applied around the upper body of the person and the ends of the fastening members are anchored to each other at the chest of the person, as shown in FIGS. 2 and 3. The anchoring of the ends of the fastening members may simply take place by means of "VELCRO" as similar type fasteners 13, 14, 15,16 provided at the ends of the fastening members in such a manner that for example the fastener 13 is outside on fastening member 3, fastener 14 is at the inside of fastening member 4, fastener 15 is at the outside of fastening member 5, and fastener 16 is at the inside of fastening member 6.

As will appear from FIG. 2 the helmet-like fastening member 7 may have a downward extension 7' at the neck portion of the person so that there will be an additional support for the neck of the person.

In addition to the above fastening members 3, 4, 5, 6 there may be provided bands 17, 18 as shown with dot-and-dash lines in FIG. 3. These will contribute to an additional attachment of the main part to the upper body and will especially counteract any transverse flexing of the injured person. The upper fastening members 3, 4 are widened upwards along the main part 1 approximately to the lower portion of the extension 7' from the helmet-like piece 7. In this way there will be an increase in the anchoring effect of the main part 1.

Figure 4:
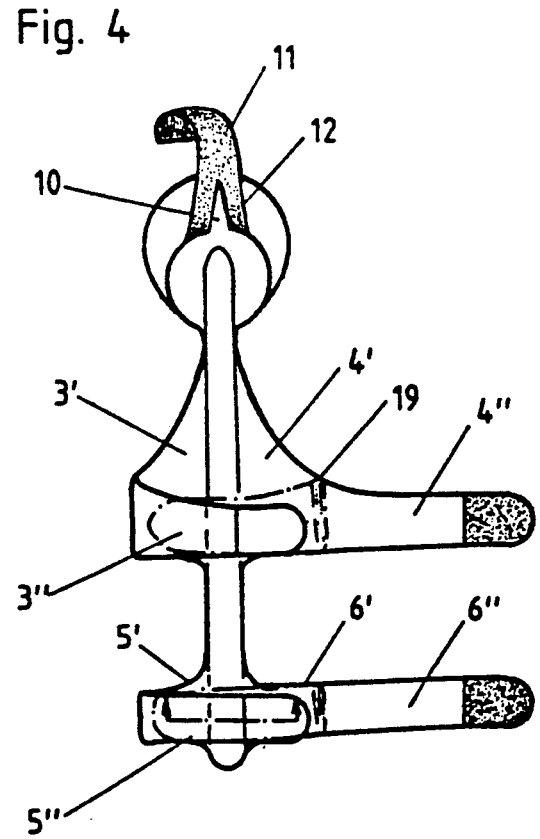
FIG. 4 is a plan view of a modified embodiment of the device according to the invention.

In FIG. 4 there is shown a modified embodiment of the device according to the invention. The fastening members 3, 4, 5, 6 are subdivided into two parts 3', 3", 4', 4", 5', 5", 6', 6" by hinge portions 19. These may be formed by embossing the plastic material. A possible embodiment may also be to make the inner parts 3', 4', 5', 6' of a textile band or ribbon material. The essential point is that at least the outer parts of fastening members 3, 4, 5, 6 consist of such a stiff material that they may be inserted behind and around an injured person without the need of lifting, pulling or twisting the person. Because of this subdivision of the fastening members 3, 4, 5, 6 these may be folded back on each other as indicated in FIG. 4, whereby also parts 4" and 6" may be folded inwards in the same way as shown at parts 3" and 5". In this manner there will be obtained a narrow package which will take very little space and thus may simply be placed for example at the rear side of the front seats in a car. Because of the slit 10 in the helmet-like fastening piece 7 this may also to a certain degree be flattened or folded out so that it may be arranged over the top of the back of the front seat.

Figure 6:
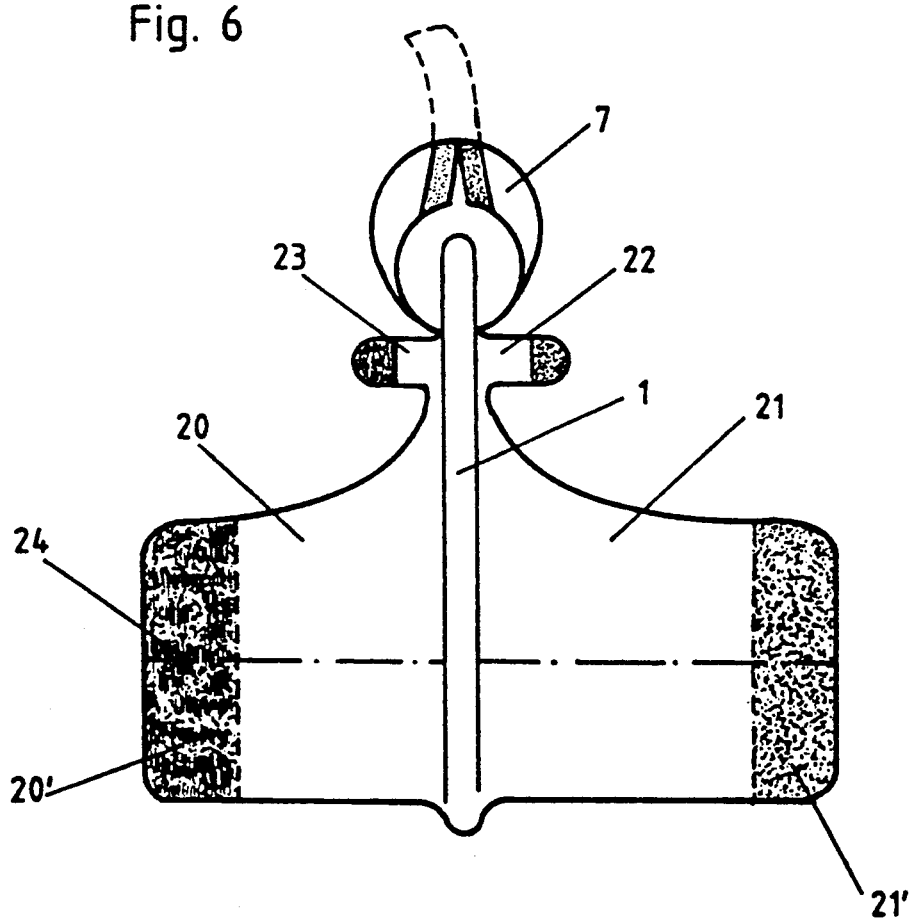
FIG. 6 is a plan view of a further embodiment according to the invention.

In FIG. 6 there is shown an embodiment with a wide fastening member 20, 21 having "VELCRO" or similar type fasteners 20', 21'. In addition to this wide fastening member which is adapted to lie around the whole chest of the patient, there are provided fastening members 22, 23 which together are intended to encircle the neck of the injured person. This leads to an enhanced anchoring of the rigid part 1 to the body of the injured person. The wide fastening members 20, 21 will be suitable for keeping bandages in position, and in serious casualties may serve to keep inner organs in position and prevent these from coming out through possible large wound openings.

The slit 10 in the helmet piece 7 is shown extending from the forward edge to at least the middle of the head. However, this slit 10 may with advantage extend right back to the upper end of main part 1. In this way the fastener piece may more easily be adjusted to the head shape and size as well as a possible head bandage. Thereby it will also be more easy to fold out this piece so that it will be more flat and can be more easily packaged and stored, for example in a vehicle or the like.

Figure 7:
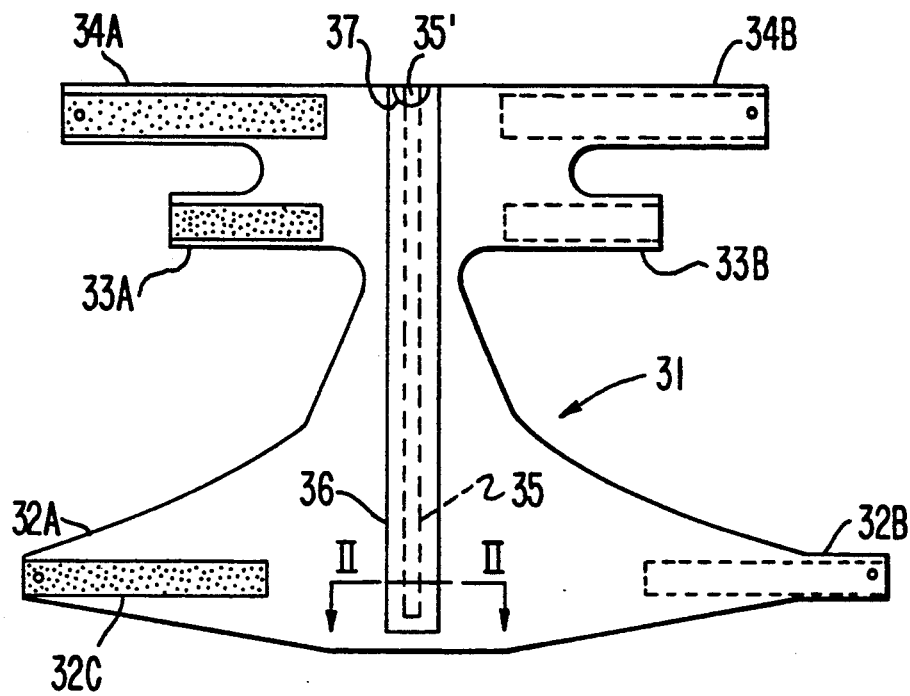
FIG. 7 is a in plan view of still another and a preferred embodiment of the device according to the invention.

The preferred embodiment of the supporting device as shown in FIG. 7 also comprises a main part or member 31 being primarily adapted to constitute a rear piece in the position of use to which the device is in particular directed. Shaped as more or less integrated parts of the main part 31 there are shown lower fastening members 32A and 32B adapted to be arranged around the abdominal or chest areas of the patient and provided with locking means, for example cooperating "VELCRO" or similar type fasteners at the outer end portions of the fastening members. One such fastener is indicated at 32C. At the upper portion of the main part 31 there are provided fastening members 33A and 33B, 34A and 34B respectively, for anchoring around the neck portion and the head respectively of the patient. As mentioned above in connection with FIGS. 1-6, such band or belt-like fastening members may be shaped and arranged in various ways so as to obtain the desired mounting of such a device to an injured person. For example some of these fastening members may extend at an inclination with respect to the central main part.

The embodiment shown in FIG. 7 may be based upon the cutting of the main part with fastening members from a single piece of a flexible sheet material, for example a suitable plastic sheet material or a textile material. This may result in a very advantageous production at the same time as favourable properties in use are obtained. The employment of essentially flexible materials in the device means that it may be easily be folded or packed together, for example to constitute a contribution to the first aid equipment in a car, as also explained above.

Figure 8:
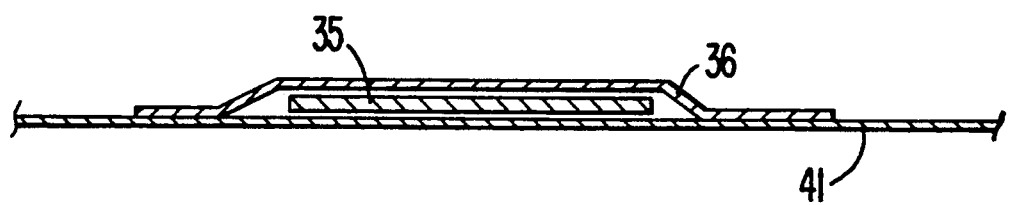
FIG. 8 is a partial section along line II—II in FIG. 7, at an enlarged scale.

In order to give the necessary stiffness or supporting effect, there is provided centrally in the longitudinal direction of the main part 31 in FIG. 7, an elongate supporting member in the form of a metal rod 35 which preferably has a flat profile or cross-sectional shape as will be seen from FIG. 8, and this metal rod extends substantially over the whole length of the device. The metal rod 35 is arranged in a pocket 36 which may consist of the same or a similar flexible material as the main part 31 and the fastening members 32A, 32B, 33A, 33B, 34A, 34B. The piece of material constituting a pocket 36 may for example be sewn or heat sealed along its edges to the sheet of material 41 (see FIG. 8) which constitutes the main part 31. An alternative form could be one in which the main part 31 and possibly the fastening members are double walled, i.e. composed of two plastic or textile sheets thereby forming the pocket for the metal rod 35 between these two sheets of material.

It is a substantial advantage that the rod 35 has a flat or plate like shape, because inter alia this shape will result in the least possible discomfort for the patient. With a suitable choice of material and dimensions the metal rod moreover and with advantage may be manually deformable so that it may be adjusted so as to give support in certain attitudes or at particular portions of an injured person. For this purpose aluminum sheet of a suitable thickness is an advantageous material for the rod 35.

As will appear from FIG. 7 the pocket 36 is open upwardly and the upper end 35' of metal rod 35 is visible in a cut-out 37 at the top of the pocket, this cut-out making it more easy to grasp the metal rod for pulling it out of the pocket when this is desirable. This is especially of interest when X-ray investigations of the patient shall take place. Depending upon material and dimensions of the metal rod 35 this may be more or less a hindrance for the X-ray investigation. In many cases it will be absolutely necessary to avoid such metal parts on the patient during the X-ray investigation. With the solution given here there cannot arise any problems in this regard.

It is obvious that a supporting or stiffening element in the form of a metal rod may also be provided detachably or insertably to such a device in other ways, for example by means of pushbutton-like elements. The solution as described, however, with a longitudinal pocket 36 is particularly advantageous.

As indicated above it may often be an advantage that one or more of the fastening members have outer portions possessing a certain stiffness for the insertion around lying or clamped persons. A particular possibility for giving one or more fastening members such stiffness may consist in supporting or stiffening elements similar to the metal rod 35, being possibly exchangeable and adapted to be inserted into pockets in the fastening members, which may suitably coincide with or may be formed by the fastener pieces indicated in FIG. 7, such as the fastener 32C.

As to the manner of using such a supporting device it is obvious that in certain cases it may be used in other ways than what is contemplated as the primary position of use, namely for fixation or support of the back and/or the neck portion of an injured person. With the deformability of the metal rod 35 as described and the flexibility of the remaining device with the various fastening members, this may also if necessary be used for the support and fixation of other body parts, for example the limbs when an accident has occurred. For example the metal rod 35 may be deflected to an approximate right angle at a middle portion thereof for the fixation of an arm in a desired position.

I claim:

1. A supporting device for use in administering first aid to a person injured in an accident, particularly to a person having a back and/or neck injury, said device comprising:
   a main member to be positioned centrally along the back of an injured person, said main member having formed therein an elongated pocket opening upwardly in the normal position of use;
   fastening members extending from said main member at positions to be mounted around the abdominal and chest area of the injured person and around the head or neck of the injured person;
   said main member and said fastening members being formed of flexible material; and
   an elongated supporting member in the form of a substantially flat metal rod accommodated in said pocket of said main member in a manner such that said metal rod may be selectively manually pulled from and pushed into said pocket, said metal rod having a length sufficient to support the back and neck of the injured person when said metal rod is within said pocket.

2. A device as claimed in claim 1, wherein said metal rod is aluminum.

3. A device as claimed in claim 1, wherein said metal rod has cross sectional dimensions sufficient to enable said metal rod to be manually deflected with resultant permanent deformation to conform to shapes of different body parts of an injured person and to have sufficient stiffness to provide support in such shapes.

4. A device as claimed in claim 1, wherein at least outer end portions of said fastening members are made of an elastic material of sufficient stiffness to enable said outer end portions to be inserted around the injured person when the injured person is in close contact with the ground or other surface.

5. A device as claimed in claim 4, wherein said outer end portions are articulated to remaining portions of said fastening members, such that said outer end portions may be folded over said remaining portions.

6. A device as claimed in claim 5, wherein said remaining portions are formed of soft flexible material.

* * * * *